US008084444B2

United States Patent
Geracioti, Jr.

(10) Patent No.: US 8,084,444 B2
(45) Date of Patent: Dec. 27, 2011

(54) TREATMENT OF DERMATITIS WITH DEHYDROEPIANDROSTERONE-GLUCOCORTICOID COMBINATIONS

(75) Inventor: Thomas D. Geracioti, Jr., Cincinnati, OH (US)

(73) Assignee: RxDino, LLC, Cincinnati, OH (US)

( * ) Notice: Subject to any disclaimer, the term of this patent is extended or adjusted under 35 U.S.C. 154(b) by 1186 days.

(21) Appl. No.: 11/108,032

(22) Filed: Apr. 15, 2005

(65) Prior Publication Data

US 2006/0069071 A1 Mar. 30, 2006

Related U.S. Application Data

(60) Provisional application No. 60/612,717, filed on Sep. 24, 2004.

(51) Int. Cl.
 *A01N 45/00* (2006.01)
 *A61K 31/56* (2006.01)
(52) U.S. Cl. .............. 514/171; 514/169; 514/170
(58) Field of Classification Search .............. 514/169, 514/170, 171
 See application file for complete search history.

(56) References Cited

U.S. PATENT DOCUMENTS

| | | | | |
|---|---|---|---|---|
| 4,496,556 | A * | 1/1985 | Orentreich | 514/178 |
| 6,479,058 | B1 * | 11/2002 | McCadden | 424/401 |
| 6,552,010 | B1 | 4/2003 | Schwartz et al. | |
| 2007/0015840 | A1 * | 1/2007 | Dalko et al. | 514/720 |

OTHER PUBLICATIONS

Wenninger et al. 1997, International Cosmetics Ingredient Dictionary and Handbook, pp. 1660-1662.*
AHFS Drug Information 2001, American Society of Health-System Pharmacists, Inc. 2001 Schimmer & Parker, Bethesda, MD.
Drake, Lynn A., et al., Guidelines of care for contact dermatitis, J Am Acad Dermatol. 1995; 32:109-13.
Bird, C.E., et al, Dehydroepiandrosterone: Kinetics of metabolism in normal men and women, J Clin Endocrinol Metab. 1978;47:818-822.
Brazzini, B., Pimpinelli, N., New and established topical corticosteroids in dermatology: clinical pharmacology and therapeutic use, Am J Clin Dermatol. 2002; 3(1):47-58.
Crawford, G.H., McGovern, T.W., Poison ivy, N Engl J Med. Nov. 21, 2002, 347(21):1723.
Gallegos, A.J., Berliner, D.L., Transformation and conjugation of dehydroepiandrosterone by human skin. J Clin Endocrinol Metab. 1967;27:1214-8.
Geracioti, T.D., DHEA supplementation of systemic glucocorticoids, International J Dermatol. 2005, in press.
Green, C., et al., Topical corticosteroids for atopic eczema: clinical and cost effectiveness of once-daily vs. more frequent use, Br J Dermatol. Jan. 2005;152(1):130-41.
Guin, J.D., Complications of topical hydrocortisone, Am Acad Dermatol. Apr. 1981;4(4):417-22.
Guin, J.D., Treatment of toxicodendron dermatitis (poison ivy and poison oak), Skin Therapy Letter, Apr. 2001;6(7):3-6.
Juckett, G., Plant dermatitis: Possible culprits go far beyond poison ivy. Postgrad Med. Sep. 1996; 100(3):159-171.
Lee, S.S., Topical steroids, International J Dermatology. Dec. 1981; 20(10):632-41.
Leung, D.Y.M., et al., New insights into atopic dermatitis, J Clin Invest. 2004;113(5):651-57.
Meding, B., Jarvholm, B., Hand eczema in Swedish adults—changes in prevalence between 1983 and 1996, J Invest Dermatol, Apr. 2002;118(4):719-23.
Pearce, D.J., et al., Class I topical corticosteroid use by psoriasis patients in an academic practice, J Dermatolog Treat. 1004;15:235-8.
Rapaport, M.J., Lebwohl, M., Corticosteroid addiction and withdrawal in the atopic: the red burning skin syndrome, Clinics in Dermatology. 2003;21:201-214.
Resnick, S.D., Poison-ivy and poison-oak dermatitis, Clinic in Dermatology. Apr.-Jun. 1986: 4(2):208-212.
Rosenfeld, B.J., et al., 24-hour secretory pattern of dehydroisonandrosterone and dehydroisoandrosterone sulfate, J Clin Endocrinol Metab. 1975;40(5):850-855.
Schimmer, B.P., Parker, K.L., Adrenocorticotropic hormone; adrenocortical steroids and their synthetic analogs; inhibitors of the synthesis and actions of adrenocortical hormones, In: Hardman JG, Limbird LE, Gilman AG, eds. Goodman & Gilman's The Pharmacologic Basis of Therapeutics, 10$^{th}$ edition. McGraw-Hill Medical Publishing Co., NY, NY, 2001, pp. 1649-1677.
Van Coevorden, A.M., et al., Overview of studies of treatments for hand eczema—the EDEN hand eczema survey, British Journal of Dermatology. 2004;151:446-451.
Van Vollenhoven, R.F., et al., Dehydroepiandrosterone in systemic lupus erythematosus: results of a double-blind, placebo-controlled, randomized clinical trial, Arthritis Rheum, Dec. 1995; 38(12):1826-1831.

* cited by examiner

*Primary Examiner* — Sreeni Padmanabhan
*Assistant Examiner* — Samira Jean-Louis
(74) *Attorney, Agent, or Firm* — Frost Brown Todd LLC

(57) ABSTRACT

Dermatitis can be effectively treated with the combined administration of dehydroepiandrosterone (DHEA) and a glucocorticoid. Systemic, topical and prepackaged DHEA-glucocorticoid embodiments are described.

24 Claims, No Drawings

TREATMENT OF DERMATITIS WITH DEHYDROEPIANDROSTERONE-GLUCOCORTICOID COMBINATIONS

CROSS-REFERENCE TO RELATED APPLICATION

This application is based upon and claims priority from U.S. Provisional Application No. 60/612,717, filed Sep. 24, 2004, incorporated herein by reference.

BACKGROUND OF THE INVENTION

Dermatitis is inflammation of the skin. Many forms and causes of dermatitis exist, including eczema, atopic dermatitis, allergic contact dermatitis, irritant contact dermatitis, psoriasis, seborrheic dermatitis, and photosensitivity dermatitis. The current invention relates to dehydroepiandrosterone-glucocorticoid combinations which are effective against these dermatoses.

Eczema is a general term for epidermal inflammation progressively characterized by erythema (redness), pruritis (itching), vesicular eruption, weeping, oozing, crusting, scaling, lichenification (skin thickening), and even increased pigmentation. Atopic dermatitis is an eczematous dermatitis in genetically predisposed individuals who have an abnormally low threshold for cutaneous pruritis and eruption.

Contact dermatitis is the most common form of dermatitis and can be either allergic, mediated by a sensitizer or allergen, or irritant. Contact dermatitis is an altered state of skin reactivity induced by exposure to an external agent (American Academy of Dermatology Association [AADA] 1995), chemical, animal, or vegetable, effecting perhaps 5 to 20% of Americans at some point in life. Allergic contact dermatitis is mediated by a delayed immune, or cell-mediated immune, response, while irritant contact dermatitis is caused by an inherently irritating property of a compound. Contact dermatitis can range in severity from a mild and short-lived, self-limited condition, to a "severe, persistent, job-threatening, and sometimes life-threatening disease" (AADA 1995). More than 2,800 substances have been identified as contact allergens (AADA 1995).

Poison ivy dermatitis is considered "the prototype allergic contact dermatitis" (Guin 2001), with the majority of Americans showing allergy to one degree or another. "Allergic contact plant dermatitis and poison ivy are nearly synonymous, at least in North America" (Juckett 1999).

Poison ivy and its relatives, including poison oak and poison sumac, are in the genus toxicodendron ("poisonous plant") of the Anacardiaceae family (Crawford and McGovern 2002). Toxicodendron contact dermatitis results from reaction to an oil-soluble "oleoresin" (urushiol) that is dispersed throughout the plants and readily absorbed by human skin (Guin 2002). The oily allergen, urushiol, can be transferred from one part of the body to another and can survive on fomites (such as garden tools or clothing) for long periods.

The clinical presentations of poison ivy, or toxicodendron, allergic contact dermatitis are well known to most Americans. These include erythematous, pruritic (red, intensely itching), blistering lesions that are often streaked across skin expanses. Vesicles usually develop within 2-3 days after exposure to urushiol plant allergen; these vesicles easily break and release "plasma" or "weep" to form a crust (Juckett 1996). Large bullous lesions often develop. Intense itching is present as a core symptom in poison ivy dermatitis and can be debilitating. Reduced pruritis-related daytime concentration and pruritis-related insomnia are common. The scratching of poison ivy lesions can lead to secondary lesions.

Once generated, primary poison ivy dermatitis lesions are usually self-limiting and clear within 3-4 weeks. However, poison ivy dermatitis may last for months and can be severe, with intensely pruritic blisters covering substantial body surface or afflicting the genitals, face, hands, or feet (Goodall 2002). Poison ivy allergic dermatitis can also be systemic, as, for example, after inhaled smoke from burned poison ivy plants.

Glucocorticoid hormones, usually synthetic, are a mainstay of treatment for contact dermatitis in general, and also, accordingly, for poison ivy (urushiol) dermatitis (AADA 1995; Juckett 1996; Brodell & Williams 1999; Goodall 2002). Topical glucocorticoids are used for mild to moderate contact dermatitis (AADA 1995), including toxicodendron dermatitis outbreaks, or for outbreaks on limited skin areas. Topical treatment alone may be adequate for mild cases of contact dermatitis. Applications are usually made two times per day, although range from one to four or more times per 24 hours. Topical glucocorticoids may suppress symptoms of allergic toxicodendron dermatitis (such as poison ivy), but do not normally shorten the 2-3 week course of dermatitis.

Systemic glucocorticoids are indicated in those patients in whom extensive skin involvement is seen or in whom symptoms are severe enough to interfere with daily function (e.g., work relationships, or sleep) (AADA 1995; Juckett 1996; Brodell & Williams 1999; Goodall 2002). In poison ivy dermatitis, and contact dermatitis in general, systemic glucocorticoids are also sometimes prescribed in order to reduce the allergic reaction and severe itching that promotes scratching, subsequent secondary lesions, and prolongation of the episode in vulnerable individuals.

Oral glucocorticoid therapy for poison ivy dermatitis is usually recommended to begin with 30-60 mg/day of prednisone, or its equivalent in glucocorticoid potency (see Table 1), and to continue for 10-21 days (Resnick 1986; Juckett 1996; Guin 2001). Accordingly, Brodell and Williams (1999) recommend starting most adults with 60 mg/day of prednisone for four days, and then tapering the dose over the next two weeks. Altogether, for most adults, they recommend using 540 mg of prednisone over 14 days of treatment. A treatment period with glucocorticoids of at least 14 days is recommended because rebound dermatitis often occurs if the duration of glucocorticoid treatment is shorter (Brodell and Williams 1999). In this regard, the commercially available prednisone or methylprednisolone prepackaged dose packs that are commonly administered for poison ivy contact dermatitis provide a total of 105 mg of prednisone (or the roughly equivalent 84 mg of methylprednisolone) in a tapering dose over six days. For severe poison ivy dermatitis these prepackaged glucocorticoids do not provide an adequate dose and the course of treatment is too brief (Juckett 1996; Brodell & Williams 1999).

| Glucocorticoid | Approximate Glucocorticoid Dose Equivalent |
|---|---|
| Cortisone | 25 mg |
| Betamethasone | 0.7 mg |
| Dexamethasone | 0.75 mg |
| Hydrocortisone | 20 mg |
| Methylprednisolone | 4 mg |
| Prednisolone | 5 mg |
| Prednisone | 5 mg |
| Triamcinolone | 0.8 mg |

References: AHFS Drug Information 2001, American Society of Health System Pharmacists, Bethesda Md., 2001; Schimmer & Parker 2001

Glucocorticoids, the steroid hydrocortisone and its derivatives, are classical "stress hormones" and have catabolic (tissue breakdown) effects. Systemic adverse effects of glucocorticoids include bone demineralization (bone thinning), body fat redistribution (trunk obesity and "moon"-like [round] face), weakening of elastic tissues and muscle, and hyperglycemia (elevated blood sugar), among others.

In addition to their use in contact dermatitis, glucocorticoids—predominantly topical—are the mainstay for treatment of eczema, hand dermatitis, psoriasis, and atopic dermatitis (Green et al 2005, Leung et al 2004, Pearce et al 2004). However, there is currently inadequate information available regarding the treatment of hand eczema, which can vary in severity from mild inflammation to severe and incapacitating blistering, scaling, and/or cracking of the whole hand and all fingers (Van Coevorden et al 2004).

Topical glucocorticoids are currently still the most frequently used drugs in dermatologic practice (Brazzini and Pimpinelli 2002), even though they were introduced back in the 1950s (Lee 1981) and have significant adverse effects. Topical glucocorticoids are well known to cause local skin atrophy (thinning of the skin), purpura (bruised-appearing skin), striae ("stretch marks"), tolerance and "addiction syndrome" (Lee 1981; Rapaport and Lebwohl 2003). Chronic use of topical glucocorticoid is ideally avoided in the treatment of atopic dermatitis, due to side effects (Leung et al 2004). However, there are few good alternatives at present. The topical calcineurin inhibitors pimecrolimus and tacrolimus were introduced in the United States in 2001 and 2002, respectively, as an alternative to topical glucocorticoids in the treatment of atopic dermatitis, but, according to the U.S. Food and Drug Administration, these drugs share "a potential cancer risk" and, according to an FDA public health Advisory issued Mar. 10, 2005, should be used only as second-line agents for the short-term and intermittent treatment of atopic dermatitis in patients who have failed or are intolerant to other treatments (www.fda.gov/cder/drug/advisory/elidel_protopic.htm).

Dehydroepiandrosterone (DHEA), interconvertible with its sulfate, dehydro-epiandrosterone-sulfate (DHEA-S), and its derivatives (e.g., the 7-hydroxylated derivative), is an adrenocortical sex hormone precursor secreted, like the adrenocortical glucocorticoid cortisol with which it shares a similar circadian rhythm, in response to corticotropin (ACTH) released by the anterior pituitary (Bethune 1975; Rosenfeld et al 1975). The average daily production of DHEA in the human is approximately 25 mg per day (Bird et al 1978) whereas the average production of hydrocortisone is about 20 mg per day (or the equivalent of about 5 mg of prednisone or 4 mg of methylprednisolone). Suprahysiologic doses of DHEA (200 mg/day) have been reported to help treat the rheumatic disease systemic lupus erythematosus (SLE) (van Vollenhoven et al 1995). In this regard, Schwartz and Gurwith (2003) taught in U.S. Pat. No. 6,552,010 that systemic lupus erythematosus (SLE) can be treated by adding DHEA, of 100 mg per day or more, to a pre-existing drug regimen consisting of either a glucocorticoid, a non-steroidal anti-inflammatory, an immunosuppressant, or an anti-malarial drug.

DHEA is present in skin (Gallegos & Berliner 1967) and DHEA replacement in situations associated with low circulating DHEA concentrations, such as in adrenal insufficiency or aging, improves skin hydration, epidermal thickness, and sebum production (Baulieu et al 2000; Johannsson 2002).

The present invention teaches that combined glucocorticoid-DHEA treatment, in various formulations (oral, topical, etc) is an effective treatment for various forms of dermatitis and is a significant improvement over the current typical treatment of a glucocorticoid alone. The present invention teaches that co-administration of DHEA with a glucocorticoid hormone in poison ivy contact dermatitis (reaction to urushiol), hand dermatitis, eczema or atopic dermatitis, and psoriasis is effective, reduces symptoms such as pruritis and rash, and shortens the duration of the dermatitis.

SUMMARY OF THE INVENTION

Combined DHEA-glucocorticoid compounds are effective pharmaceutical treatments for dermatitis, including allergic contact dermatitis, irritant contact dermatitis, hand dermatitis, eczema, atopic dermatitis, and psoriasis. The treatment is comprised of a dehydroepiandrosterone-glucocorticoid combination in various embodiments, including those administered either topically or systemically (Geracioti, 2005, in press). These DHEA-glucocorticoid combinations reduce the symptoms of dermatitis, including itching (pruritis) and discomfort, and hasten the recovery from dermatitis. Embodiments of the DHEA-glucocorticoid combination disclosed include DHEA-glucocorticoid compositions for topical administration and prepackaged DHEA-glucocorticoid regimens for oral use.

DETAILED DESCRIPTION OF THE INVENTION

Various embodiments of DHEA-glucocorticoid combinations for the treatment of dermatitis are described below. The first clinical examples show that in individuals highly sensitive to the toxicodendron allergen urushiol, contact dermatitis is resolved relatively quickly during co-administration of DHEA and a glucocorticoid. After that, prepackaged "dose pack" embodiments of the DHEA-glucocorticoid combination, for systemic administration, are described. Next, topical DHEA-glucocorticoid compositions—for application directly to the skin—are described, along with clinical examples showing efficacy of combined DHEA and a glucocorticoid, applied topically, in irritant and allergic contact dermatitis, hand dermatitis, eczema/atopic dermatitis, and psoriasis.

EXAMPLE 1

A 45-year-old white male, with a long history of hypersensitivity to poison ivy and many episodes of severe poison ivy contact dermatitis, lasting more than two weeks each, presented with a pruritic facial eruption involving approximately 15% of his face two days after having walked through a wooded area. The patient had first noticed a single, pruritic eruption in the left lower mandibular area the night before presentation, which he attributed to a mosquito bite. In the morning he shaved using an electric razor. By late afternoon intensely pruritic, erythematous vesicular poison-ivy-like lesions had erupted on the face, within the shaved surface space, particularly in the left lower mandibular area, where one blister was 5.5 cm×2 cm. A diagnosis of poison ivy dermatitis was made and both prednisone and DHEA were prescribed. 30 mg of prednisone and 50 mg of DHEA were taken orally before bed and the next morning the patient states that he was shocked to find that the dermatitis had largely resolved and the remaining lesions were barely raised, dry, and non-pruritic. He took 20 mg of prednisone and 50 mg of DHEA in the a.m. Even though he reported total resolution of the dermatitis, the next morning he ingested 10 mg of prednisone and 25 mg of DHEA, as prescribed. Examination in the late afternoon revealed no active facial dermatitis beyond areas of rough, dry skin.

EXAMPLE 2

A 38-year-old white female, with a history of poison ivy dermatitis, presented in the morning one day after the onset of worsening, pruritic, erythematous poison ivy-like lesions on both forearms and upper legs, with each limb showing one or more blisters of at least 4 cm×3 cm. Two days before she had spent considerable time in a wooded area. Upon presentation she scratched all affected areas vigorously, including her upper legs lesions through polyester pants. A diagnosis of poison ivy dermatitis was made and the patient was prescribed a tapering oral dose of 40 mg-30 mg-20 mg-10 mg of prednisone per day (morning dosing), with the first day's dose to be taken immediately. She was simultaneously prescribed four days of oral DHEA 50 mg-50 mg-50 mg-25 mg (first dose as soon as possible, then morning dosing). Examination on the fourth day revealed total resolution of the dermatitis on both arms; the extent and inflammatory appearance of the poison ivy lesions were both reduced by 50 to 60% on the upper legs. Pruritis was reportedly reduced as well. No adverse effects of the hormone regimen were endorsed or reported.

EXAMPLE 3

The morning after a 35-year-old man, with an impressive history of poison ivy dermatitis, wandered into a wooded area in order to retrieve a ball, he developed pruritic, poison ivy-like (streaked) lesions over his left medial ankle area and lower leg. The following day, two days after exposure, he presented with a taut, bullous lesion on the ankle approximately 2×2×2 cm. Smaller vesicular lesions encircled this lesion. A diagnosis of poison ivy dermatitis was made. The bullous lesion was drained. Topical steroids were applied to the affected area, which was then bandaged lightly to prevent irritation by trousers. A 30 mg dose of prednisone and a 50 mg dose of DHEA were prescribed to be taken orally right away. The patient indicated that the next morning the poison ivy dermatitis was substantially improved, as judged by the absence of pruritis and the apparent resolution of visible lesions; he took 20 mg of prednisone and 50 mg of DHEA. The next morning the patient took 10 mg of prednisone and 25 mg of DHEA; removal of the bandage that day showed no evidence of active inflammation, only dry, hardened skin of the affected area.

The above clinical examples used 125 to 175 mg of DHEA total, over 2-4 days, in combination with 60 to 100 mg of prednisone, total, over the same time period. The maximum doses used in any 24-hour period were 100 mg of DHEA and 50 mg of prednisone—in examples 1 and 3. In example 2, 100 mg of prednisone and 175 mg of DHEA over four days yielded an excellent but incomplete response, indicating that higher and/or longer dosing would have been preferable. Because allergic contact dermatitis varies in severity, the optimal course of DHEA-glucocorticoid therapy will also vary. Thus, the present invention encompasses daily oral DHEA doses of from about 0.1 to about 300 mg in combination with daily glucocorticoid doses of from about 1 to about 60 mg of prednisone equivalents. Systemic (for example, oral) DHEA and glucocorticoid therapy may be needed for 14 days or more in the most severe cases of contact dermatitis. However, the current invention teaches that a DHEA-glucocorticoid combination can be effective over shorter durations of therapy.

Dose Packs

DHEA-glucocorticoid prepackaged dose packs for use in the treatment of severe dermatitis, including allergic contact dermatitis, constitute an element of the present invention. 21-tablet, prepackaged "dose packs" of the glucocorticoids methylprednisolone and prednisone have long been available on the U.S. market. These glucocorticoid dose packs provide a total of 110 mg of prednisone or 88 mg of prednisolone over six days, using a tapering dose schedule wherein 30 mg of prednisone (or 24 mg of methylprednisolone) are administered the first day and only 5 mg of prednisone (or 4 mg of methylprednisolone) are given on the 6$^{th}$ day. These doses have been criticized as too low and the taper course has been criticized as too short to treat severe allergic poison ivy dermatitis (Brodell and Williams 1999). However, by co-administering DHEA as taught herein, the doses and 6-day tapering course of a glucocorticoid dose pack containing a total of 88 mg of prednisolone or its equivalent become more effective more often.

The following examples describe some DHEA-glucocorticoid dose packs. However, a practitioner familiar with the art will know that permutations of the dosage strength, times of administration, and days of therapy will vary according to the clinical circumstance at hand and far exceed the few examples given. Daily doses will range from 0.1 mg to 300 mg of DHEA—most typically 2.5 mg to 240 mg—and from 1 to 100 mg of prednisone equivalents—most typically from about 2.5 mg to 60 mg (about 2 to 44 mg per day of methylprednisolone, or the equivalent). The number of prepackaged dosing days will range from 3 to 14. A consistent, rather than a tapering, dosing schedule may be used. Moreover, the combination of each dose of DHEA and a glucocorticoid into a single oral formulation can be achieved using accepted pharmaceutical vehicles. Instructions for use will be printed on the various embodiments of the DHEA-glucocorticoid dose pack. The tablets, capsules, or other pharmaceutically acceptable oral formulations will be readily removable by patients, for example punched out, from standard card-like containers or dispensers.

TABLE 1

Example of a 6-day DHEA-glucocorticoid dose pack for oral administration. In this example, thirteen 25-mg DHEA tablets or capsules and twenty-one 4-mg methylprednisolone tablets (or the glucocorticoid dose equivalent) are prepackaged into a tapering 6-day course.

|  | Before breakfast | After Lunch | After Supper | Before Bed |
|---|---|---|---|---|
| Day 1 | ○○ XX | ○ | ○ | ○○ XX |
| Day 2 | ○ X | ○ | ○ | ○○ XX |
| Day 3 | ○ X | ○ | ○ | ○ X |
| Day 4 | ○ X | ○ |  | ○ X |
| Day 5 | ○ X |  |  | ○ X |
| Day 6 | ○ X |  |  |  |

○ = Prednisolone 4 mg tablets or methylprednisolone 4 mg tablets (or the dose equivalent of another glucocorticoid, such as about 5 mg of prednisone). Tablets = a pharmaceutically acceptable oral formulation
X = DHEA 25 mg tablets (or capsules, or another pharmaceutically acceptable oral formulation)

Total in the above example=350 mg DHEA and 88 mg methylprednisolone equivalents (about 100 mg of prednisone) over 6 days.

TABLE 2

Example of a 7-day DHEA-glucocorticoid dose pack.

| | AM | PM |
|---|---|---|
| Day 1 | ○○○○○○ XX | ○○ XX |
| Day 2 | ○○○○ XX | ○○ XX |
| Day 3 | ○○○○ X | ○ X |
| Day 4 | ○○○ X | ○ X |
| Day 5 | ○○ X | ○ X |
| Day 6 | ○○ X | |
| Day 7 | ○ X | |

○ = Prednisone 5 mg (or its approximate dose equivalent, for example, methylprednisolone 4 mg or hydrocortisone 20 mg)
X = DHEA 25 mg tablet, capsule, or other oral formulation Total in the above example=145 mg prednisone equivalents and 400 mg DHEA, in a tapering dose given over 6 days:

TABLE 3

Another embodiment of the DHEA-glucocorticoid dose pack involves exclusive morning administration of DHEA and a glucocorticoid

| | AM |
|---|---|
| Day 1 | ○○○○○○○○ XXXX |
| Day 2 | ○○○○○○ XXXX |
| Day 3 | ○○○○○ XX |
| Day 4 | ○○○○ XX |
| Day 5 | ○○○ XX |
| Day 6 | ○○ X |
| Day 7 | ○ X |

○ = prednisone 5 mg or its equivalent (such as methylprednisolone 4 mg)
X = DHEA 25 mg

TABLE 4

In another embodiment, a 10-day DHEA-glucocorticoid dose pack with morning dosing

| | AM |
|---|---|
| Day 1 | ○○○○○○○○ XXXX |
| Day 2 | ○○○○○○ XXXX |
| Day 3 | ○○○○○○ XXXX |
| Day 4 | ○○○○ XX |
| Day 5 | ○○○○ XX |
| Day 6 | ○○○○ XX |
| Day 7 | ○○○○ XX |

TABLE 4-continued

In another embodiment, a 10-day DHEA-glucocorticoid dose pack with morning dosing

| | AM |
|---|---|
| Day 8 | ○○○ X |
| Day 9 | ○○ X |
| Day 10 | ○ X |

○ = Prednisone 5 mg for oral administration, or the equivalent
X = DHEA 25 mg for oral administration or the equivalent FIG. 5. 3 day "DHEA-glucocorticoid mini-dose pack"

| | AM |
|---|---|
| Day 1 | ○○○○○○ XXXX |
| Day 2 | ○○○○ XX |
| Day 3 | ○○ X |

○ = Prednisone 5 mg for oral administration, or the equivalent
X = DHEA 25 mg for oral administration, or the equivalent DHEA-Glucocorticoid Preparations for Topical Use The present invention includes topical DHEA-glucocorticoid preparations (such as creams, gels, ointments, lotions, powders, sprays, grease, liquids, paste, shake lotion, or patches or combinations thereof, formulated using conventional, compatible pharmaceutically acceptable vehicles) wherein, in the compositions, the percentage DHEA by weight ranges from about 0.01 to about 20% and the glucocorticoid ranges from about 0.01 to about 10% by weight in hydrocortisone equivalents. For mild cases, a topical preparation of about 1% DHEA and about 1% hydrocortisone, applied to affected skin one to four times per day, is sufficient. For more severe cases, a higher potency DHEA-glucocorticoid topical treatment (or systemic treatment) is indicated, such as a topical formulation of hydrocortisone 2.5%-DHEA 2.5%.

DHEA and glucocorticoids are steroids that can be incorporated into lipophilic carriers in the concentrations specified, in accordance with conventional pharmaceutical formulation standards and vehicles. Powdered hydrocortisone and powdered DHEA (or the micronized steroids), which are biochemically similar and share dissolution properties, can be easily mixed into a stable emollient cream vehicle or into white petrolatum. For example, 0.01-10% DHEA and hydrocortisone 0.01 to 10% can be mixed into white petrolatum to form an ointment. Alternatively, 0.01 to 10% by weight of each of the powder forms of DHEA and hydrocortisone can be mixed into white petrolatum and light mineral oil. Other glucocorticoids can be substituted for hydrocortisone in equivalent potency ratios.

Other carrier, vehicle, or excipient ingredients, which are known to those of ordinary skill in the art, may be used to form variant creams, ointments, lotions, tinctures, emulsions, gels, sprays, or shake lotions. In addition, those additives or adjuvants that are commonly included in topical compositions, including lipophilic or hydrophilic gelling agents, moisturizers, preservatives, solvents, antioxidants, emulsifying agents, fragrances, fillers, colorants, humectants, and screening agents, can be included in the DHEA-glucocorticoid topical formulation in conventional proportions, generally ranging from about 0.01 to about 20%, by weight. Additionally, the DHEA-glucocorticoid topical preparation described here can be prepared with supplemental ingredients, including, but not limited to, analgesics, anesthetics, antihistamines, antibacterials, antifungals, antivirals, antiyeasts, anti-inflammatory agents, anti-pruritic agents, calamine, drying agents, moisturizing agents (aloe vera and others), other antipsoriatic agents, antiaging and antiwrinkle agents, antiatrophy agents, astringents, vitamins (vitamin E, D, C and others), elements, minerals (zinc and others), hormones, peptides, probiotics, elastins, retinoids, salts, colloidal oatmeal, or mixtures thereof.

DHEA, or a derivative, can be added to existing, commercially available glucocorticoid topical formulations, including to many 0.25 to 1% (by weight) hydrocortisone creams and ointments that are currently available over-the-counter (without a prescription). These include, but are not limited to, those over-the-counter creams and ointments produced or distributed by Johnson & Johnson, Pfizer Healthcare (Morris Plains, N.J.), CVS, Walgreen's, and The Kroger Co. (Cincinnati, Ohio). Usually the DHEA will be added in a powdered or micronized form. DHEA can also be mixed into existing prescription topical glucocorticoid products.

Hand eczema (hand dermatitis) is common worldwide with a one-year prevalence of about 1% (Meding and Jarvholm 2002), yet no standard, effective treatment has been identified (Van Coevorden et al 2004). Hand eczema can be caused by contact irritants, contact allergens, atopic, "endogenous" or unknown factors, or, presumably, by some combination of allergic, irritant, and endogenous factors (Van Coevorden et al 2004). Psoriasis is a chronic dermatitis that responds only moderately well to glucocorticoids; yet, due to limited effective alternatives, most patients with psoriasis receive topical glucocorticoid therapy which "will likely remain a mainstay of psoriasis therapy" (Pearce et al 2004).

EXAMPLE 4

To make a 30 gram tube of DHEA 2.5%-triamcinolone 0.1% cream, 0.03 grams of powdered triamcinolone acetonide and 0.75 grams of powdered DHEA are weighed, wetted with 0.5 mL ethoxy diglycol and mixed into an emollient cream base according to the suggested specifications of the Professional Compounding Centers of America (PCCA, Houston, Tex.).

A 31-year-old white female had chronic hand and finger dermatitis (hand eczema), most likely related to irritant or allergic reaction to food preparation and dish washing in combination with endogenous factors (given her history of atopic dermatitis). One 2.5 cm by 3 cm erythematosus, scaling area was treated with the DHEA 2.5%-triamcinolone 0.1% cream via application of a thin layer twice per day, while two other similar areas were left untreated. Examination after two days of treatment (after four applications) showed complete resolution of the dermatitis formerly in the treated area but persistence of the untreated areas of dermatitis. Subsequent application of the DHEA 2.5%-triamcinolone acetonide 0.1% cream to the other affected areas resulted in the resolution of dermatitis within another two days.

EXAMPLE 5

A 30 gram jar of DHEA 1%-hydrocortisone 1% cream is made by mixing 0.3 grams of powdered DHEA and 0.3 grams of powdered hydrocortisone into a commercially-available vanishing cream base consisting of propylene glycol, stearyl alcohol, cetyl alcohol, sorbitan monostearate, polysorbate 60, mineral oil, and purified water (Hawkins Inc., Minneapolis Minn.).

A 42-year-old white female with chronic elbow psoriasis for more than 20 years, had applied over-the-counter 1% hydrocortisone creams to the psoriatic area once or twice daily for at least five years in an attempt at treatment. She stated that the 1% hydrocortisone creams helped control the extent of the lesion, but did not resolve it—nor did chronic cream application eliminate the pain she felt when the elbow was touched, bumped, or rested (on a table, for example). Moreover, she complained that the skin in the affected area had become thinner with chronic hydrocortisone use.

Examination revealed an inflamed, raised, irregular, moist, erythematosus lesion, approximately 6 cm by 5 cm, of the skin over the left elbow—present despite a history of years of daily 1% hydrocortisone cream application. Twice daily application of a thin film of the DHEA 1%-hydrocortisone 1% cream to the affected area was prescribed. Follow-up examination after one week of treatment revealed a dry lesion that had was substantially less erythematosus and reduced in extent by approximately 20%. The patient claimed that the pain and tingling that she had chronically experienced were no longer present. After 30 days of treatment, examination revealed a flat, dry 4-cm by 3-cm lesion with minimal erythema. The patient reported that these results with the DHEA 1%-hydrocortisone 1% cream were substantially better than she had ever achieved with a hydrocortisone 1% cream whose active ingredient was hydrocortisone alone.

EXAMPLE 6

30 gram tubes of 2.5% DHEA—2.5% hydrocortisone ointment are prepared by mixing 0.75 grams of DHEA and 0.75 grams of hydrocortisone powder into white petrolatum (soft paraffin).

A 47-year-old white male with a history of presumed atopic dermatitis (eczema), characterized by erythematosus, pruritic patches on the abdomen used the DHEA 2.5%-hydrocortisone 2.5% ointment twice a day after a recurrence of an irregular erythematosus patch, about 5 cm by 4 cm, on the left upper quadrant of the abdomen. The dermatitis improved on day one and resolved totally in approximately three days.

EXAMPLE 7

A 30-gram jar of DHEA 5% and hydrocortisone 5% is made by mixing 0.3 grams of powdered DHEA and 0.3 grams of powdered hydrocortisone into a commercially-available vanishing cream base consisting of propylene glycol, stearyl alcohol, cetyl alcohol, sorbitan monostearate, polysorbate 60, mineral oil, and purified water (Hawkins Inc., Minneapolis Minn.).

A 53 year-old white male in generally good health acutely developed an extensive, intensely pruritic rash covering his neck, chest, both arms, and upper legs. The etiology of the rash was not definitively established, but the patient had that morning used his wife's new body lotion, which he denied ever having done before. Moreover, he had also for the first time that day worn clothes washed in an unfamiliar (new for the patient) laundry detergent. In addition to recommendation of avoidance of the possible irritants or allergens, a thin film of the DHEA 5%-hydrocortisone 5% was applied at night to some of the erythematous, pruritic areas and these areas were markedly improved the next morning compared with the nontreated areas. A second application was administered on the second night, and the rash was almost entirely resolved by the next day.

EXAMPLE 8

A 30-gram tube of DHEA 2.5%-Hydrocortisone 2.5% ointment is prepared as in EXAMPLE 6. A 41-year-old white female had chronic, severe contact dermatitis on her ring finger and surrounding areas due to an undiagnosed gold allergy. In addition to erythema, swelling, and miniature vesicles, two splits in the dermis, of approximately one cm each, were apparent on the ring finger. Intense pruritis and burning were also reported. Secondary worsening of the lesion due to scratching was acknowledged. The patient applied a thin film of the ointment twice per day. Significant improvement in the dermatitis was apparent at the one-day follow-up and substantial resolution was documented at the 3-day follow-up. Pain and burning were absent.

OTHER DHEA-GLUCOCORTICOID EMBODIMENTS

Various modifications of the current invention will be obvious to those with skill in the art. To those with ordinary skill in the art, claims involving specific glucocorticoids can be seen to be clearly applicable to various permutations of the base molecule. For example, in claiming hydrocortisone, derivatives and pharmaceutically acceptable salts, such as hydrocortisone acetate, hydrocortisone butyrate, hydrocortisone-17-butyrate-21-propionate, hydrocortisone probutate, hydrocortisone sodium phosphate, hydrocortisone proloutate, and hydrocortisone valerate are also claimed. Betamethasone also includes betamethasone dipropionate, betamethasone valerate, and so on. DHEA, as used herein, is also intended to encompass its derivatives (including, for example, sulfated derivatives) and pharmaceutically acceptable salts (including, for example, 7-alpha-hydroxy-DHEA, 7-beta-hydroxy-DHEA, 7-oxo-DEHA, epiandrosterone, 16-bromoepiandrosterone, and 16-alpha-fluoro-5-androster-17-one). Similarly, DHEA and a glucocorticoid can be combined in topical vehicles beyond creams and ointments, as those with ordinary skill in the art can also use foams, sprays, gels, pastes, lotions, and other topical vehicles.

Examples of glucocorticoids which can be used in the present invention include alclomethasone, amicinonide, beclomethasone, betamethasone, budesonide, clobetasol, clobetasone, clocortolone, desonide, desoximetasone, desoxymethasone, dexamethasone, diflorasone, diflucortolone, fluocinolone, fluocinonide, flurandrenolide, flurandrenolone, fluticasone, fluocortolone, flumethasone, halcinonide, halobetasol, hydrocortisone, mometasone, prednicarbate, triamcinolone, pharmaceutically acceptable salts thereof, and combinations thereof.

What is claimed is:

1. A method of treating dermatitis in a mammal by administering to said mammal a composition comprising from about 0.01% to about 20% of said composition by weight of dehydroepiandrosterone (DHEA), or DHEA derivatives, and a therapeutically effective amount of a glucocorticoid.

2. The method of claim 1 wherein the dermatitis is contact dermatitis due to allergic or irritant sensitivity to contact with allergens or irritants selected from those derived from plants, textiles, metals, animals/insects, food, detergents, cosmetics, fragrances and perfumes, adhesives, medications, solvents, and other chemicals.

3. The method of claim 2 wherein the contact dermatitis is caused by poison ivy or poison oak.

4. The method of claim 1 wherein the dermatitis is selected from eczema, atopic dermatitis, psoriasis, seborrheic dermatitis, phototoxic dermatitis, and lichenoid dermatitis.

5. The method of claim 1 wherein said DHEA-glucocorticoid combination is administered orally, topically, sublingually, transdermally, subcutaneously, parentally, intranasally, via inhalation, or combinations thereof.

6. The method of claim 1 wherein the dermatitis is either local or systemic.

7. The method of claim 1 comprising oral administration of DHEA in combination with an oral glucocorticoid.

8. The method of claim 7 wherein the glucocorticoid is selected from alclomethasone, amicinonide, beclomethasone, betamethasone, budesonide, clobetasol, clobetasone, clocortolone, desonide, desoximetasone, desoxymethasone, dexamethasone, diflorasone, diflucortolone, fluocinolone, fluocinonide, flurandrenolide, flurandrenolone, fluticasone, fluocortolone, flumethasone, halcinonide, halobetasol, hydrocortisone, mometasone, prednicarbate, triamcinolone, pharmaceutically acceptable salts thereof, pharmaceutically acceptable derivatives thereof, and mixtures thereof.

9. The method of claim 7 wherein the DHEA and a glucocorticoid are combined into a single tablet, capsule, gel, or vehicle suitable for oral administration.

10. The method of claim 7 wherein DHEA and glucocorticoid are administered via a prepackaged dose pack.

11. The method of claim 10 wherein the DHEA-glucocorticoid dose pack comprises three to 14 days of administration.

12. The method of claim 1 wherein DHEA is combined in a topical formulation with a glucocorticoid using a pharmacologically acceptable vehicle.

13. The method of claim 12 wherein the glucocorticoid is selected from alclomethasone, amicinonide, beclomethasone, betamethasone, budesonide, clobetasol, clobetasone, clocortolone, desonide, desoximetasone, desoxymethasone, dexamethasone, diflorasone, diflucortolone, fluocinolone, fluocinonide, flurandrenolide, flurandrenolone, fluticasone, fluocortolone, flumethasone, halcinonide, halobetasol, hydrocortisone, mometasone, prednicarbate, triamcinolone, pharmaceutically acceptable salts thereof, pharmaceutically acceptable derivatives thereof, and combinations thereof.

14. The method of claim 12 wherein the DHEA-glucocorticoid combination is topically administered via cream, gel, ointment, lotion, foam, powder, spray, grease, liquid, emulsion, paste, shake lotion, patch, liposomes, microparticles, or combinations thereof.

15. The method of claim 7 wherein the daily dose of DHEA ranges from about 0.1 mg to about 300 mg, and the daily dose of a glucocorticoid ranges from prednisone dose equivalents of about 1 mg to about 100 mg.

16. The method of claim 12 wherein, in the topical formulation, the glucocorticoid comprises dose equivalents of hydrocortisone of from about 0.01 to about 10% by weight.

17. The method of claim 1 wherein the DHEA material is DHEA or DHEA-sulfate.

18. The method of claim 1 where the DHEA material is selected from 7-hydroxylated derivatives of DHEA, 7-oxygenated derivatives of DHEA, DHEA-sulfate, and mixtures thereof.

19. A dose pack comprising sufficient DHEA oral unit doses and sufficient glucocorticoid oral unit doses for about three to about fourteen days of administration, packaged together with instructions for administration.

20. A topical pharmaceutical composition for the treatment of dermatitis comprising from about 0.01% to about 20%, by weight, of DHEA, a safe and effective amount of a glucocorticoid, and a pharmaceutically acceptable topical carrier or vehicle.

21. The topical pharmaceutical composition according to claim 20 in the form selected from creams, gels, ointments, lotions, foams, sprays, powders, greases, liquids, emulsions, pastes, shake lotions, patches, liposomes, microparticles, and combinations thereof.

22. The topical pharmaceutical composition according to claim 21 which additionally comprises effective amounts of adjunct ingredients selected from moisturizers, vitamins, minerals, emollients, humectants, viscosity control agents, preservatives, colorants, perfumes, and combinations thereof.

23. The method of claim 1 wherein the glucocorticoid is selected from prednisone, prednisolone, methylprednisolone, and mixtures thereof.

24. The topical pharmaceutical composition of claim 20 wherein the glucocorticoid is selected from prednisone, prednisolone, methylprednisolone, and mixtures thereof.

* * * * *